United States Patent
Hoffman et al.

(10) Patent No.: US 8,483,353 B2
(45) Date of Patent: *Jul. 9, 2013

(54) INTEGRATED X-RAY DETECTOR ASSEMBLY AND METHOD OF MAKING SAME

(75) Inventors: David Michael Hoffman, New Berlin, WI (US); Jeffrey Alan Kautzer, Pewaukee, WI (US)

(73) Assignee: General Electric Company, Schenectady, NY (US)

( * ) Notice: Subject to any disclaimer, the term of this patent is extended or adjusted under 35 U.S.C. 154(b) by 286 days.

This patent is subject to a terminal disclaimer.

(21) Appl. No.: 12/967,097

(22) Filed: Dec. 14, 2010

(65) Prior Publication Data
US 2011/0080994 A1    Apr. 7, 2011

Related U.S. Application Data

(63) Continuation-in-part of application No. 11/523,359, filed on Sep. 19, 2006, now Pat. No. 7,974,377.

(51) Int. Cl.
*A61B 6/03* (2006.01)
(52) U.S. Cl.
USPC ............................................ 378/19; 378/98.8
(58) Field of Classification Search
USPC .................. 378/4–20, 98.8; 250/370.09
See application file for complete search history.

(56) References Cited

U.S. PATENT DOCUMENTS

| | | | |
|---|---|---|---|
| 4,709,382 A | 11/1987 | Sones | |
| 5,223,717 A | 6/1993 | Charpak | |
| 6,041,097 A * | 3/2000 | Roos et al. | 378/62 |
| 6,421,412 B1 | 7/2002 | Hsieh et al. | |
| 7,016,455 B2 | 3/2006 | Bruder et al. | |
| 7,019,303 B2 | 3/2006 | Homme et al. | |
| 7,039,153 B2 | 5/2006 | Bruder et al. | |
| 7,356,115 B2 | 4/2008 | Ford et al. | |
| 7,426,260 B2 | 9/2008 | Cantu et al. | |
| 2003/0002626 A1 | 1/2003 | Hoheisel et al. | |
| 2003/0123718 A1 | 7/2003 | Edic et al. | |
| 2004/0109532 A1 | 6/2004 | Ford et al. | |
| 2006/0086905 A1 * | 4/2006 | Fritzler et al. | 250/363.05 |
| 2010/0150305 A1 | 6/2010 | Nowak et al. | |

* cited by examiner

*Primary Examiner* — Hoon Song
(74) *Attorney, Agent, or Firm* — Ziolkowski Patent Solutions Group, SC

(57) ABSTRACT

An x-ray detector assembly includes a first curvilinear detector assembly comprising a first plurality of detector modules, a second curvilinear detector assembly comprising a second plurality of detector modules, and a first flat panel digital projection detector arranged between the first and second curvilinear detector assemblies such that a first end of the first flat panel digital projection detector is coupled to an inner end of the first curvilinear detector assembly and a second end of the first flat panel projection detector is coupled to an inner end of the second curvilinear detector assembly.

20 Claims, 8 Drawing Sheets

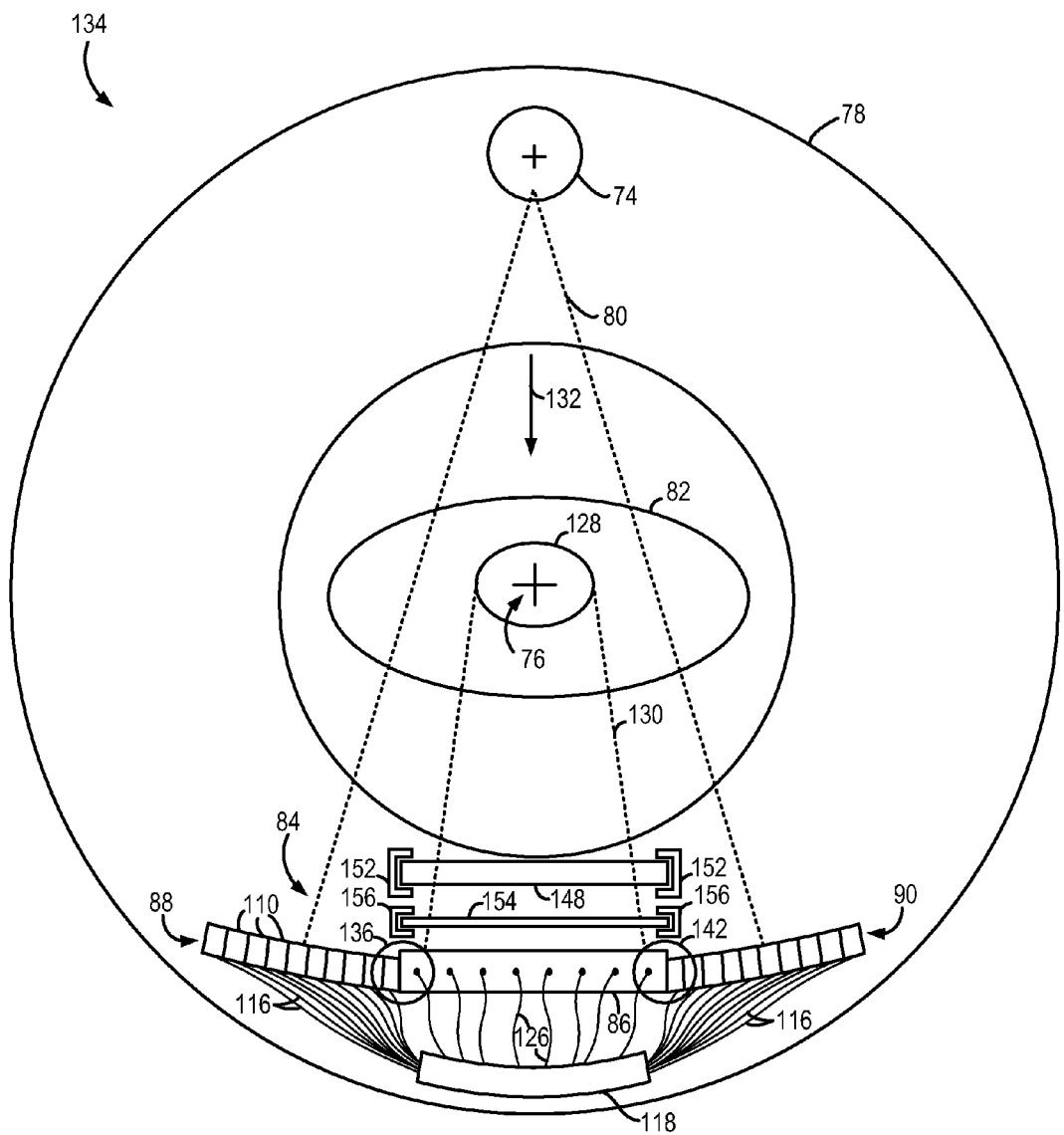
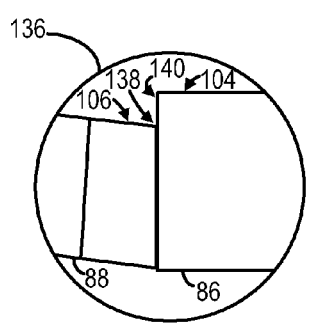
FIG. 10
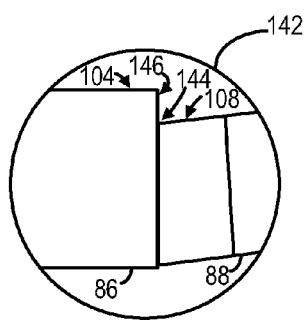
FIG. 11
FIG. 9

INTEGRATED X-RAY DETECTOR ASSEMBLY AND METHOD OF MAKING SAME

CROSS-REFERENCE TO RELATED APPLICATION

The present application is a continuation-in-part of, and claims priority to, U.S. non-provisional application Ser. No. 11/523,359, filed Sep. 19, 2006, the disclosure of which is incorporated herein by reference.

BACKGROUND OF THE INVENTION

Embodiments of the invention relate generally to diagnostic imaging methods and apparatus, and more particularly, to an apparatus and method of manufacturing an integrated x-ray detector assembly.

Typically, in CT imaging systems, an x-ray source emits a fan-shaped beam toward a subject or object, such as a patient or a piece of luggage. Hereinafter, the terms "subject" and "object" shall include anything capable of being imaged. Generally, the x-ray source and the detector assembly are rotated about the gantry within an imaging plane and around the subject. X-ray sources typically include x-ray tubes, which emit the x-ray beam at a focal point. The beam, after being attenuated by the subject, impinges upon an array of radiation detectors.

The detector assembly is typically made of a plurality of detector modules. Data representing the intensity of the received x-ray beam at each of the detector elements is collected across a range of gantry angles. The intensity of the attenuated beam radiation received at the detector array is typically dependent upon the attenuation of the x-ray beam by the subject. Each detector element of the detector array produces a separate electrical signal indicative of the attenuated beam received by each detector element. The electrical signals are transmitted to a data processing system for analysis that ultimately produces an image.

Conventional CT systems emit an x-ray with a polychromatic spectrum. The x-ray attenuation of each material in the subject depends on the energy of the emitted x-ray. If CT projection data is acquired at multiple x-ray energy levels or spectra, the data contains additional information about the subject or object being imaged that is not contained within a conventional CT image. For example, spectral CT data can be used to produce a new image with x-ray attenuation coefficients equivalent to a chosen monochromatic energy. Such a monochromatic image includes image data where the intensity values of the voxels are assigned as if a CT image were created by collecting projection data from the subject with a monochromatic x-ray beam. Spectral CT data facilitates better discrimination of tissues, making it easier to differentiate between materials such as tissues containing calcium and iodine, for example.

A principle objective of energy sensitive scanning is to obtain diagnostic CT images that enhance information (contrast separation, material specificity, etc.) within the image by utilizing two or more scans at different chromatic energy states. High frequency generators have made it possible to switch the kVp potential of the high frequency electromagnetic energy projection source on alternating views. As a result, data for two or more energy sensitive scans may be obtained in a temporally interleaved fashion rather than two separate scans made several seconds apart as typically occurs with previous CT technology. The interleaved projection data may furthermore be registered so that the same path lengths are defined at each energy level using, for example, some form of interpolation.

Conventional curvilinear detector array include a large number of individual detector elements arranged on the detector array. The detector elements are scintillator/photodiode cells arranged in two-dimensional modules that are then combined into two-dimensional detector area arrays. The coverage area of the detector array is defined by the number of detector elements in each 2D module and the number of 2D modules that are combined to form the detector assembly.

While known systems and methods that include conventional curvilinear detector arrays can be employed to acquire projection data at multiple x-ray energy levels or spectra and display, the coverage area of a scan is defined by the size of the detector array. Because each individual detector element has its own element-specific readout channel, the larger the detector assembly the more costly and complex the imaging system becomes.

For various imaging applications, such as cardiac scanning, it would be advantageous to acquire all of the image data for the object being imaged in a single rotation of the gantry. Such an image data acquisition technique has a number of benefits, including minimizing motion artifacts, as an example. However, the coverage area of the detector assembly must be sized based on the size of the projection of the object being imaged on the detector array. A curvilinear detector assembly designed with a large enough coverage area to image a heart, for example, would be extremely complex and cost prohibitive.

Therefore, it would be desirable to design an x-ray detector assembly that overcomes the aforementioned drawbacks.

BRIEF DESCRIPTION OF THE INVENTION

In accordance with one aspect of the invention, an x-ray detector assembly includes a first curvilinear detector assembly comprising a first plurality of detector modules, a second curvilinear detector assembly comprising a second plurality of detector modules, and a first flat panel digital projection detector arranged between the first and second curvilinear detector assemblies such that a first end of the first flat panel digital projection detector is coupled to an inner end of the first curvilinear detector assembly and a second end of the first flat panel digital projection detector is coupled to an inner end of the second curvilinear detector assembly.

In accordance with another aspect of the invention, a method of manufacturing a detector assembly includes providing a first flat panel detector having a top surface configured to face an x-ray source, a first side surface extending from the top surface of the first flat panel detector to a bottom surface opposite the top surface, and a second side surface opposite the first side surface and extending from the top surface to the bottom surface. The method also includes providing a first curvilinear detector array having a plurality of detectors arranged therein, the first curvilinear detector array comprising a top surface configured to face the x-ray source, and aligning the first curvilinear detector array with the first flat panel detector such that an edge of the top surface of the first curvilinear detector abuts the first side surface of the first flat panel detector. Further, the method includes providing a second curvilinear detector array having a plurality of detectors arranged therein, the second curvilinear detector array comprising a top surface configured to face the x-ray source, and aligning the second curvilinear detector array with the first flat panel detector such that an edge of the top surface of the second curvilinear detector abuts the second side surface of the first flat panel detector.

In accordance with another aspect of the invention, a CT system includes a rotatable gantry having an opening therein for receiving an object to be scanned and a table positioned within the opening of the rotatable gantry and moveable through the opening in a z-direction. The CT system also includes an x-ray source coupled to the rotatable gantry and configured to project a beam of x-rays toward the object to be scanned, and a detector assembly positioned to receive the beam of x-rays from the x-ray source. The detector assembly includes a first curvilinear detector assembly comprising a plurality of detectors, a second curvilinear detector assembly comprising a plurality of detectors, and a first flat panel digital detector arranged between the first and second curvilinear detector assemblies such that a first end of the first flat panel digital detector is coupled to an inner end of the first curvilinear detector assembly and a second end of the first flat panel detector is coupled to an inner end of the second curvilinear detector assembly.

Various other features and advantages will be made apparent from the following detailed description and the drawings.

BRIEF DESCRIPTION OF THE DRAWINGS

The drawings illustrate preferred embodiments presently contemplated for carrying out the invention.

In the drawings:

FIG. 9 is a cross-sectional view of a portion of an imaging system with a detector assembly in accordance with another embodiment of the invention.

FIG. 10 is a magnified view of a portion of the detector assembly of FIG. 9.

FIG. 11 is a magnified view of another portion of the detector assembly of FIG. 9.

DETAILED DESCRIPTION

The operating environment of the invention is described with respect to a sixty-four-slice computed tomography (CT) system. However, it will be appreciated by those skilled in the art that the invention is equally applicable for use with other multi-slice configurations. Moreover, the invention will be described with respect to the detection and conversion of x-rays. However, one skilled in the art will further appreciate that the invention is equally applicable for the detection and conversion of other high frequency electromagnetic energy. The invention will be described with respect to a "third generation" CT scanner, but is equally applicable with other CT systems.

In addition, certain embodiments of the present invention provide systems, methods, and computer instructions for acquiring multi-energy data, such as dual energy data, for example. Certain multi-energy data can be used in spectral imaging systems, such as photon counting systems, for example. Dual energy data, which is a type of multi-energy data, can be embodied in monochromatic images, material density images, and/or effective-Z images. While many of the embodiments described herein are discussed in connection with dual energy data, the embodiments are not limited to dual energy data and can be used in connection with other types of multi-energy data, as one skilled in the art will appreciate.

Figure 1:
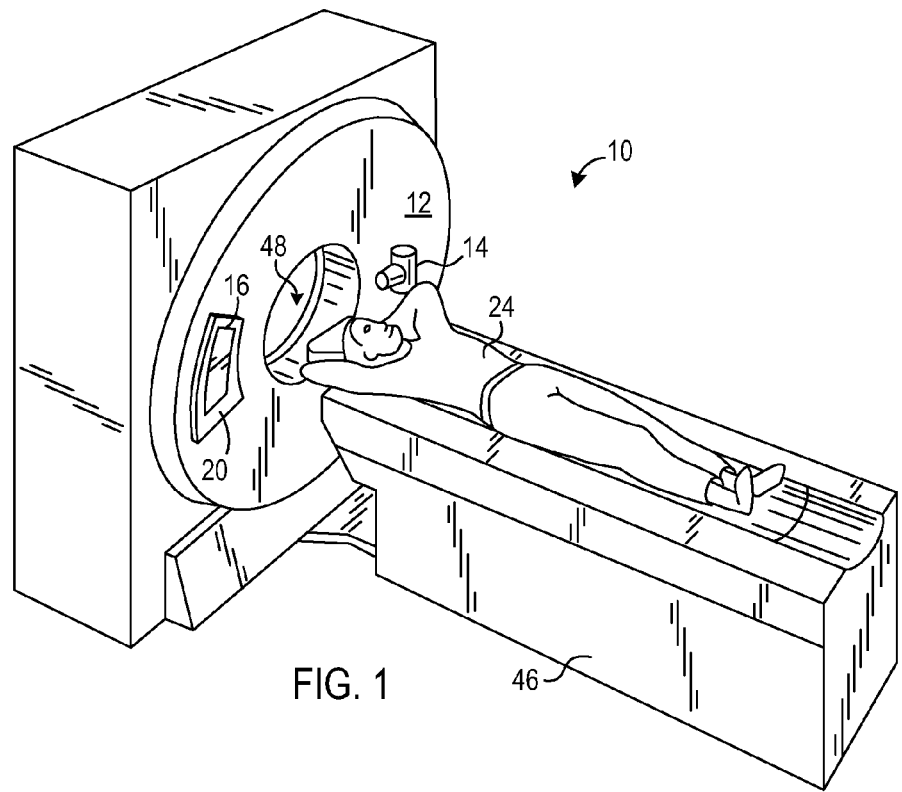
FIG. 1 is a pictorial view of a CT imaging system.
Figure 2:
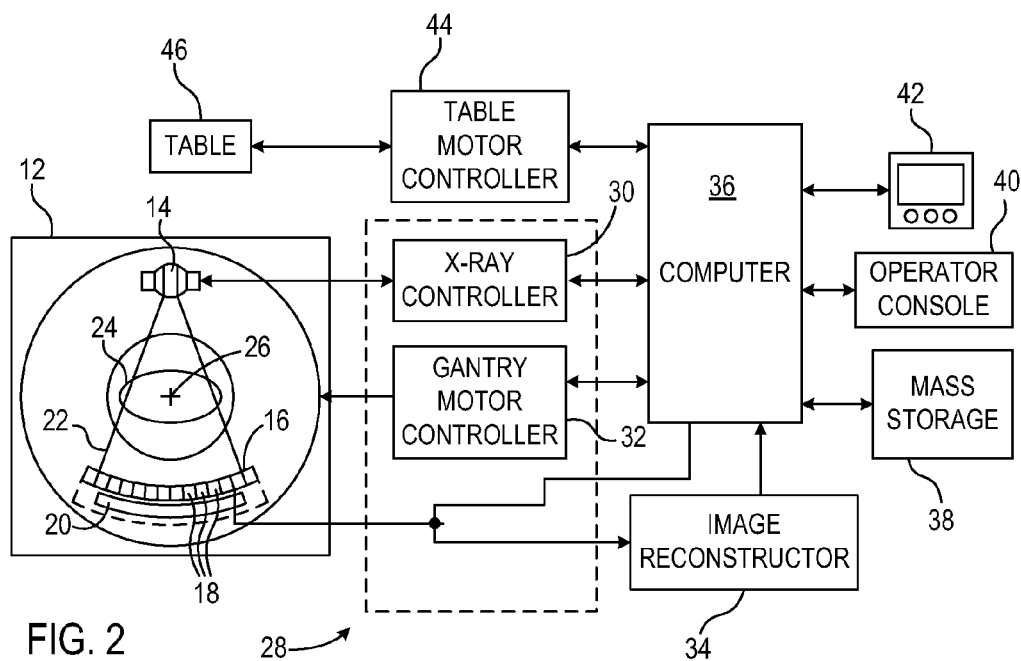
FIG. 2 is a block schematic diagram of the system illustrated in FIG. 1.

Referring to FIG. 1, a CT imaging system 10 is shown as including a gantry 12 representative of a "third generation" CT scanner. Gantry 12 has an x-ray source 14 that projects a beam of x-rays toward a detector assembly or collimator 16 on the opposite side of the gantry 12. Referring now to FIG. 2, detector assembly 16 is formed by a plurality of detectors or detector modules 18 and data acquisition systems (DAS) 20. The plurality of detectors 18 sense the projected x-rays 22 that pass through a medical patient 24, and DAS 20 converts the data to digital signals for subsequent processing. Each detector 18 produces an analog electrical signal that represents the intensity of an impinging x-ray beam and hence the attenuated beam as it passes through the patient 24. During a scan to acquire x-ray projection data, gantry 12 and the components mounted thereon rotate about a center of rotation 26.

Rotation of gantry 12 and the operation of x-ray source 14 are governed by a control mechanism 28 of CT system 10. Control mechanism 28 includes an x-ray controller 30 that provides power and timing signals to an x-ray source 14 and a gantry motor controller 32 that controls the rotational speed and position of gantry 12. An image reconstructor 34 receives sampled and digitized x-ray data from DAS 20 and performs high speed reconstruction. The reconstructed image is applied as an input to a computer 36 which stores the image in a mass storage device 38.

Computer 36 also receives commands and scanning parameters from an operator via console 40 that has some form of operator interface, such as a keyboard, mouse, voice activated controller, or any other suitable input apparatus. An associated display 42 allows the operator to observe the reconstructed image and other data from computer 36. The operator supplied commands and parameters are used by computer 36 to provide control signals and information to DAS 20, x-ray controller 30 and gantry motor controller 32. In addition, computer 36 operates a table motor controller 44 which controls a motorized table 46 to position patient 24 and gantry 12. Particularly, table 46 moves patients 24 through a gantry opening 48 of FIG. 1 in whole or in part.

Figure 3:
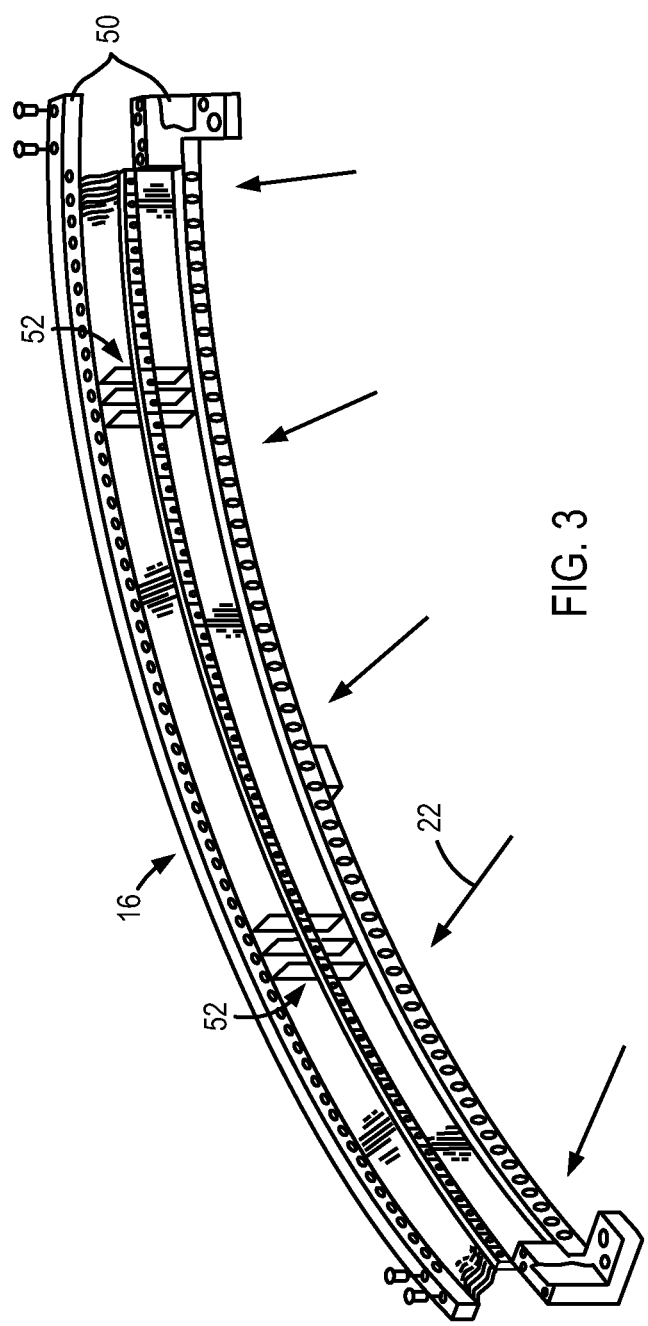
FIG. 3 is a perspective view of one embodiment of a CT system detector array.

As shown in FIG. 3, detector assembly 16 includes rails 50 having collimating blades or plates 52 placed therebetween. Plates 52 are positioned to collimate x-rays 22 before such beams impinge upon, for instance, detector 18 of FIG. 4 positioned on detector assembly 16. In one embodiment, detector assembly 16 includes 57 detectors 18, each detector 18 having an array size of 64×16 of pixel elements 54. As a result, detector assembly 16 has 64 rows and 912 columns (16×57 detectors) which allows 64 simultaneous slices of data to be collected with each rotation of gantry 12.

Figure 4:
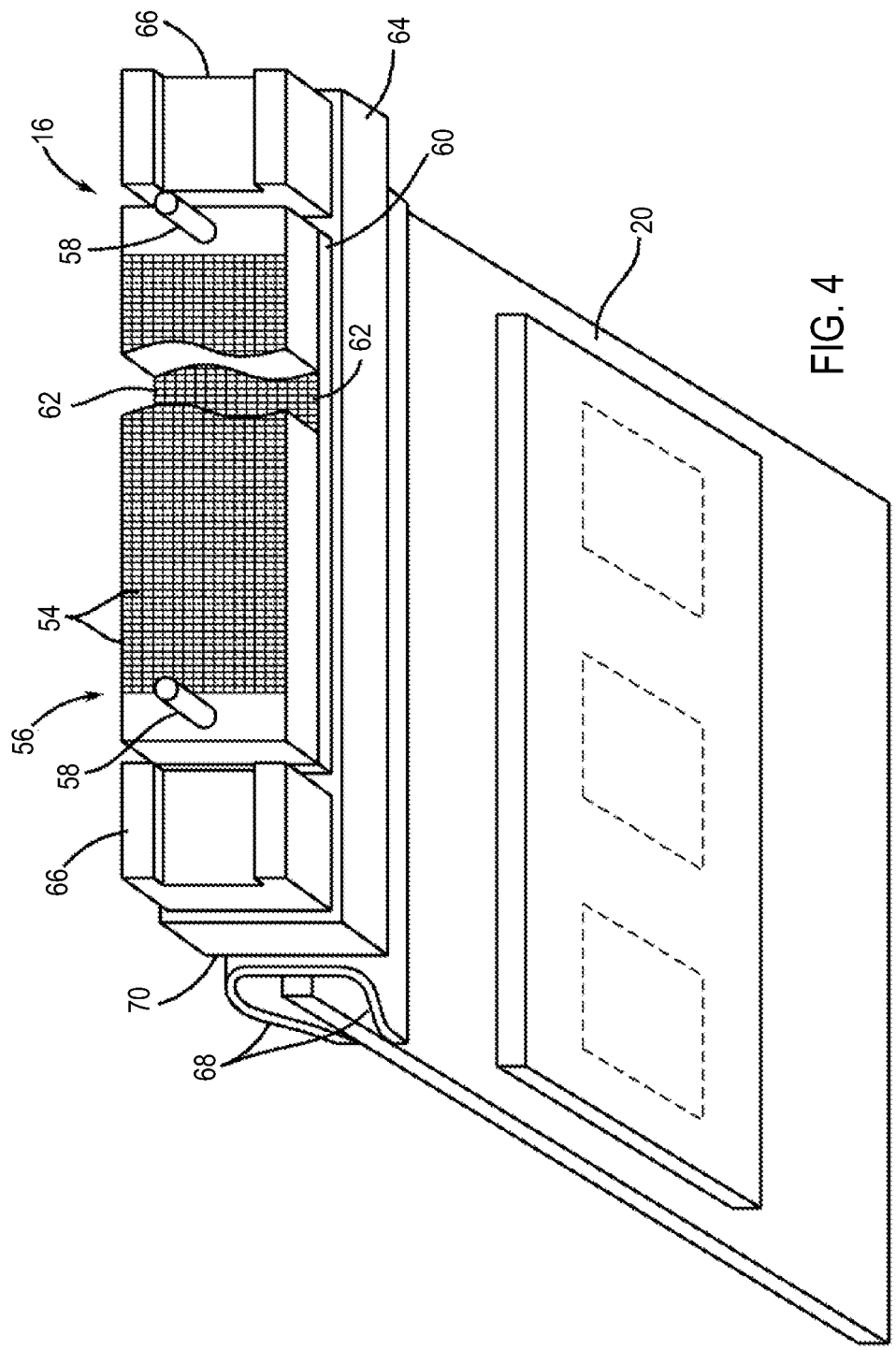
FIG. 4 is a perspective view of one embodiment of a detector.

Referring to FIG. 4, detector 18 includes DAS 20, with each detector 18 including a number of detector elements 54 arranged in pack 56. Detectors 18 include pins 58 positioned within pack 56 relative to detector elements 54. Pack 56 is positioned on a backlit diode array 60 having a plurality of diodes 62. Backlit diode array 60 is in turn positioned on multi-layer substrate 64. Spacers 66 are positioned on multi-layer substrate 64. Detector elements 54 are optically coupled to backlit diode array 60, and backlit diode array 60 is in turn electrically coupled to multi-layer substrate 64. Flex circuits 68 are attached to face 70 of multi-layer substrate 64 and to DAS 20. Detectors 18 are positioned within detector assembly 16 by use of pins 58.

In the operation of one embodiment, x-rays impinging within detector elements 54 generate photons which traverse pack 56, thereby generating an analog signal which is detected on a diode within backlit diode array 60. The analog signal generated is carried through multi-layer substrate 64, through flex circuits 68, to DAS 20 wherein the analog signal is converted to a digital signal.

Figure 5:
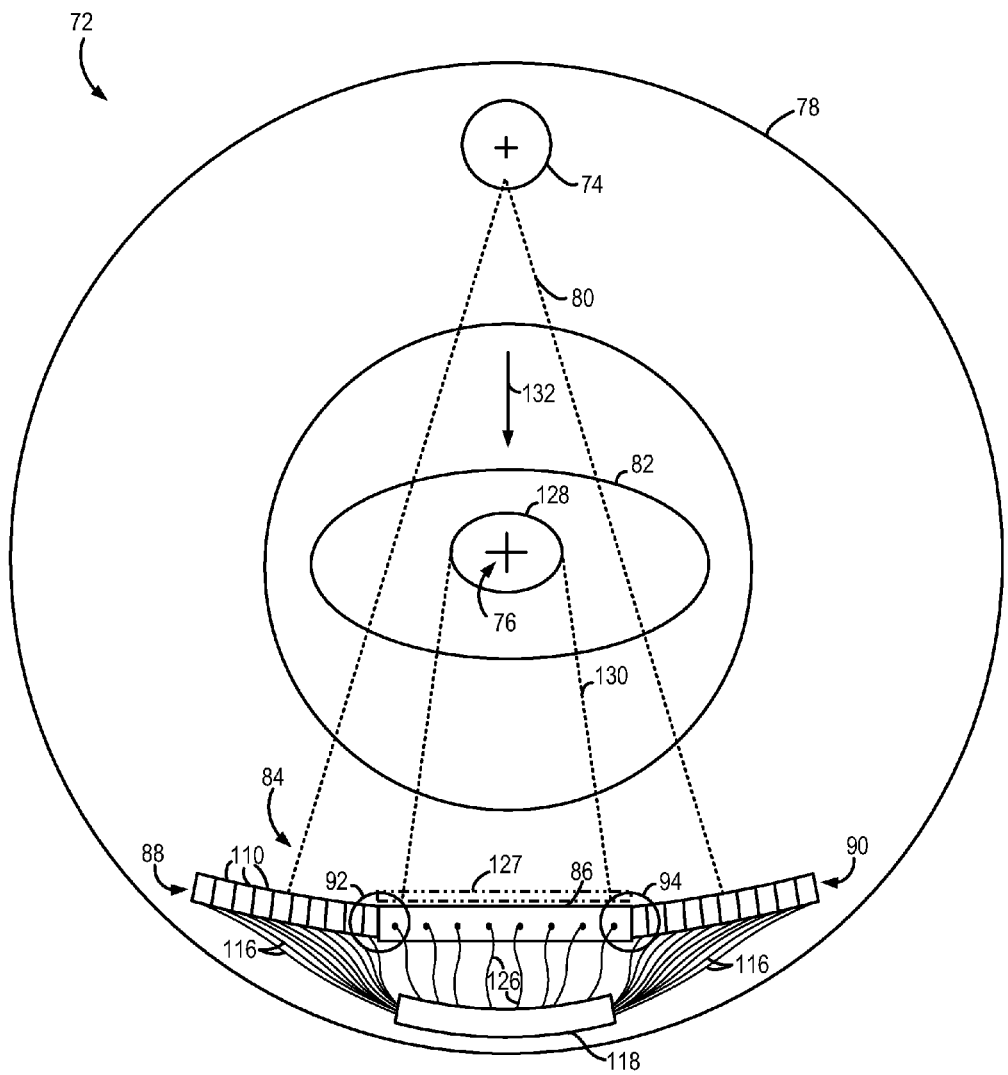
FIG. 5 is a cross-sectional view of a portion of an imaging system with a detector assembly in accordance with an embodiment of the invention.

FIG. 5 illustrates a side view diagram of a portion of an imaging system 72, such as, for example, CT imaging system 10 of FIG. 1. Imaging system 72 includes an x-ray source 74 that is configured to rotate about a center of rotation 76 of a rotatable gantry 78. A beam of x-rays 80 is produced when high-speed electrons emitted from x-ray source 74 impact the surface of a target portion (not shown) of x-ray source 74. Beam of x-rays 80 passes through a patient 82 and impinges upon a detector assembly 84.

Figure 6:
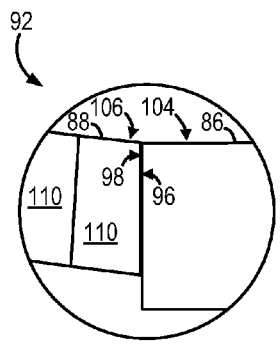
FIG. 6 is a magnified view of a portion of the detector assembly of FIG. 5.
Figure 7:
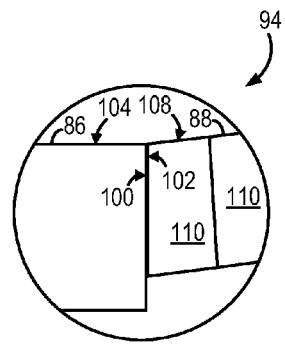
FIG. 7 is a magnified view of another portion of the detector assembly of FIG. 5.

Referring now to FIGS. 5-8, detector assembly 84 includes a flat panel digital projection radiographic detector 86 positioned between a pair of curvilinear detector assemblies or arrays 88, 90. FIG. 6 is a magnified view of a portion 92 of detector assembly 84 illustrating the interface between flat panel detector 86 and curvilinear detector assembly 88; FIG. 7 is a magnified view of a portion 94 of detector assembly 84 illustrating the interface between flat panel detector 86 and curvilinear detector assembly 90. As shown in FIG. 6, flat panel detector 86 is coupled to curvilinear detector assembly 88 such that a left surface or end 96 of flat panel detector 86 is coupled to an inside surface or end 98 of curvilinear detector assembly 88. Flat panel detector 86 is coupled to curvilinear detector assembly 90 in a similar manner, such that a right surface or end 100 of flat panel detector 86 is coupled to an inside surface or end 102 of curvilinear detector assembly 90, as shown in FIG. 7. In one embodiment, flat panel detector 86 and curvilinear detector assemblies 88, 90 are aligned such that a top surface 104 of flat panel detector 86 is substantially aligned with top surfaces 106, 108 of respective curvilinear detector assemblies 88, 90. Alternatively, top surface 104 of flat panel detector 86 may be offset from top surfaces 106, 108 of curvilinear detector assemblies 88, 90, as described in detail below with respect to FIGS. 9-10.

Each curvilinear detector assembly 88, 90 includes a plurality of individual detectors 110 each having a number of detector elements (not shown), similar to detector elements 54 of detector 18 (FIG. 4). In one embodiment, each detector 110 has a width of approximately 16 mm, measured in the x-direction (channel direction) 112, and a height of approximately 64 mm, measured in the z-direction (slice direction) 114. A readout channel 116 transmits electrical signals for each detector 110 from a respective detector 110 to a data acquisition system 118. Data acquisition system 118 converts the data to digital signals. The digital signals are transmitted to an image reconstructor, such as image reconstructor 34 (FIG. 2) for reconstruction, which may apply advanced calibration and corrections to account for interference at the interfaces between flat panel digital detector 86 and curvilinear detector assemblies 88, 90.

Figure 8:
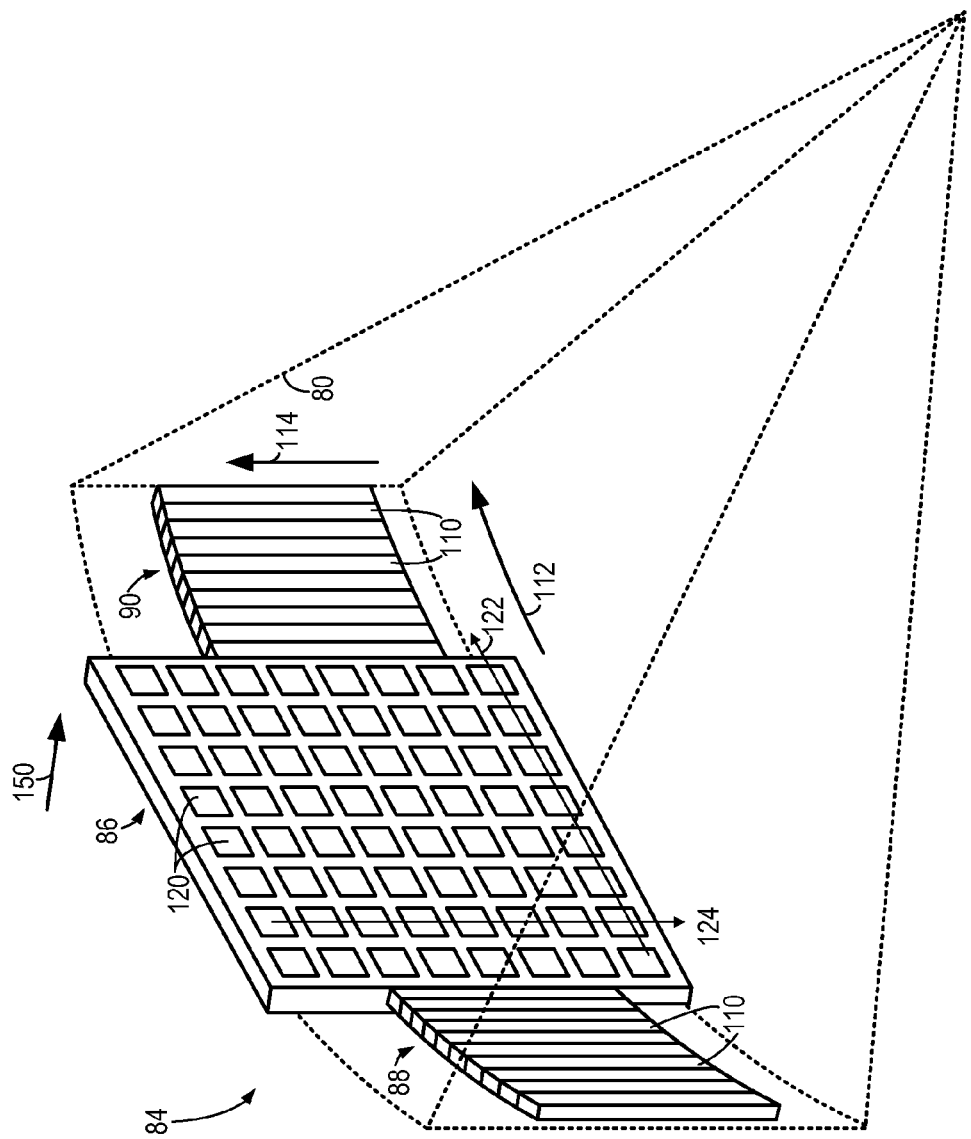
FIG. 8 is a perspective view of the detector assembly of FIG. 5 in accordance with an embodiment of the invention.

Flat panel detector 86 is a solid state digital projection radiographic detector such as a digital fluoroscopy panel typically used for catheter imaging. Flat panel detector 86 that includes an array of pixels 120 arranged in rows and columns. Unlike a conventional curvilinear detector assembly, such as detector assemblies 88, 90, pixels 120 of flat panel detector 86 are associated with a matrix of scan lines 122 and read lines 124, as shown in FIG. 8. Flat panel detector 86 includes a single readout channel 126 per read line 124. In one embodiment, flat panel detector 86 is a Revolution™ XR/d detector commercially available from the GE Healthcare business of General Electric Company.

Detector assembly 84 is aligned with x-ray source 74 such that beam of x-rays 80 passes through medical patient 82 and impinges upon flat panel detector 86 and curvilinear detector assemblies 88, 90. As shown in FIG. 5, flat panel detector 86 is aligned with a region of interest 128 of patient 82 and is sized such that a full projection 130 of region of interest 128 impinges upon flat panel detector 86. The coverage area of flat panel detector 86 at least equal to size of the projection 130 of region of interest 128 to ensure that x-rays traveling in an x-ray penetration direction 132 and passing through region of interest 128 impinge upon flat panel detector 86. Thus, flat panel detector 86 may be the size of (or slightly larger than) a projected organ of interest, such as a heart, liver, or lung according to various embodiments. In one embodiment, flat panel detector 86 has a coverage area of approximately 20 cm by 20 cm measured in the x- and z-directions 112, 114. Thus, the portion of beam of x-rays 80 that impinges upon on curvilinear detector assemblies 88, 90 corresponds to regions of patient 82 outside region of interest 128. Optionally, a flat panel collimator assembly or grid 127 (shown in phantom) may be positioned in front of flat panel detector 86 in the x-ray penetration direction 132 for collimating x-ray beams received at flat panel detector 86.

According to various embodiments, region of interest 128 corresponds to an organ being imaged, such as a heart, lung, or liver as examples. Thus, for a cardiac scanning application where the region of interest 128 is defined as the heart, a whole heart of an adult may be scanned during a single rotation of rotatable gantry 78, since the coverage area of flat panel detector 86 is larger than the projection 130 of the heart on flat panel detector 86.

Referring now to FIG. 9, an imaging system 134 is shown according to an alternative embodiment. Imaging system 134 is configured in a similar manner as described with respect to imaging system 72 of FIG. 5 in that imaging system 134 includes x-ray source 74 positioned to direct beam of x-rays 80 toward detector assembly 84, which includes a flat panel detector 86 positioned between first and second curvilinear detector assemblies 88, 90.

FIG. 10 is a magnified view of a portion 136 of detector assembly 84 illustrating the interface between flat panel detector 86 and curvilinear detector assembly 88. As shown, flat panel detector 86 is coupled to curvilinear detector assembly 88 such that an edge 138 of the top surface 106 of curvilinear detector assembly 88 abuts a first side surface 140 of flat panel detector 86. Likewise, FIG. 11 is a magnified view of a portion 142 of detector assembly 84 illustrating the interface between flat panel detector 86 and curvilinear detector assembly 90. Flat panel detector 86 is coupled to curvilinear detector assembly 90 in a similar manner as curvilinear detector assembly 88. That is, an edge 144 of top surface 108 of curvilinear detector assembly 90 abuts a second side surface 146 of flat panel detector 86.

Referring back to FIG. 9, in addition to the components included in imaging system 72 (FIG. 5), imaging system 134 includes a second flat panel digital projection radiographic detector 148 that is positioned in front of flat panel digital projection radiographic detector 86 in the x-ray penetration direction 132, such that a portion of the beam of x-rays 80 emitting from x-ray source 74 pass through second flat panel detector 148 prior to impinging upon flat panel detector 86. Flat panel detectors 86, 148 may be constructed having different attenuation characteristics, according to various embodiments. For example, the scintillators of flat panel detectors 82, 148 may have different thicknesses (measured in the y-direction 150) or be made with different scintillator materials such that flat panel detector 148 absorbs lower-energy x-rays and flat panel detector 86 absorbs higher-energy x-rays. Imaging system 134 may also include a collimating assembly or grid (not shown), similar to optional collimating assembly 127 (FIG. 5), positioned in front of each flat panel detector 86, 148.

Figure 12:
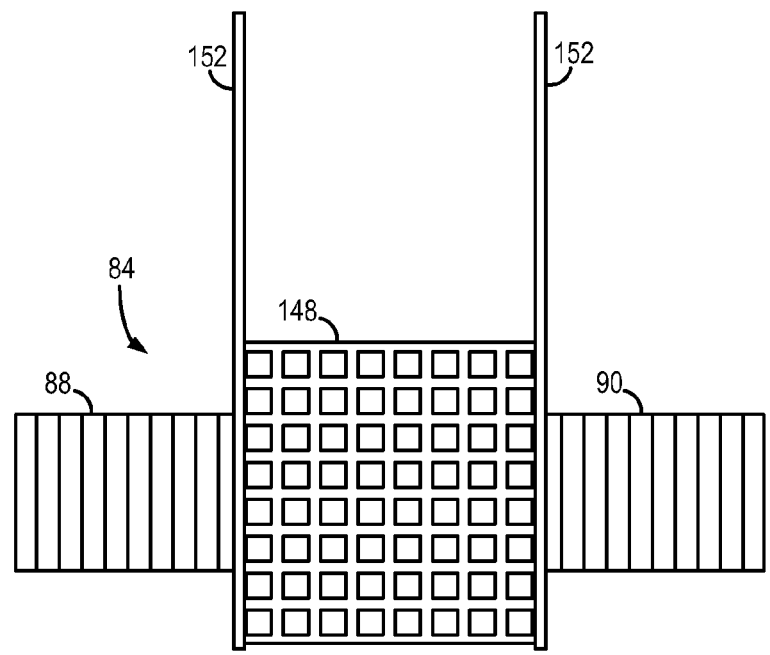
FIG. 12 is a block schematic diagram of the detector assembly of FIG. 9 illustrating a flat panel detector in a first position.
Figure 13:
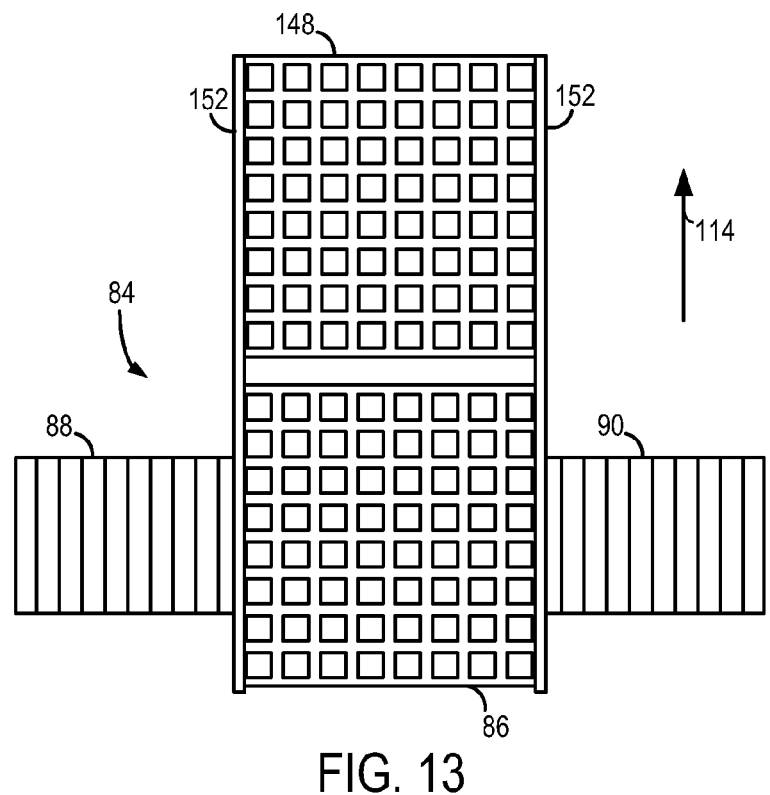
FIG. 13 is another block schematic diagram of the detector assembly of FIG. 9 illustrating the flat panel detector in a second position.

In one embodiment, second flat panel detector 148 is slidably mounted on guide rails 152, which allow second flat panel detector 148 to be moved into and out of beam of x-rays 80, as shown in FIGS. 12 and 13. Referring first to FIG. 12, a block schematic diagram of detector assembly 84 is illustrated with second flat panel detector 148 in a first position, wherein second flat panel detector 148 is positioned above and substantially overlaps flat panel digital projection radiographic detector 86, thus flat panel detector 86 is hidden from view in FIG. 12. When second flat panel detector 148 is in this first position, a portion of x-rays 80 emitting toward flat panel detector 86 are absorbed by second flat panel detector 148, while another portion of x-rays 80 pass through second flat panel detector 148 and impinge upon flat panel detector 86. FIG. 13 illustrates second flat panel detector 148 after being moved along guide rails 152 into a second position, wherein second flat panel detector 148 is offset from flat panel detector 86 in the z-direction 114. Thus, when second flat panel detector 148 is in the second position, x-rays 80 directed in the x-ray penetration direction 132 impinge upon flat panel detector 86 without first passing through second flat panel detector 148.

Referring again to FIG. 9, a notch filter 154 may be positioned between the first and second flat panel detectors 86, 148 in the x-ray penetration direction 132, for use in energy discrimination computed tomography (EDCT) applications. Notch filter 154 is constructed of an x-ray attenuating material that provides for a greater energy separation band or notch between the higher energy x-rays and the lower energy x-rays in the band of x-rays 80 emitted from x-ray source 74. According to various embodiments, notch filter 154 may be constructed of a single material or a composite material to broaden the width of the notch of filtered x-rays. Further, imaging system 72 may include a number of interchangeable notch filters 154 having different filtering properties, which can be selected based on the specifications of a given scan. Notch filter 154 may be slidably mounted on guide rails 156, in a similar manner as described above with respect to second flat panel detector 148. One skilled in the art will recognize that an imaging system may include a pair of flat panel detectors, similar to detectors 86, 148, without a notch filter, according to an alternative embodiment. Further, notch filter 154 may be positioned between patient 82 and second flat panel detector 148.

By incorporating a flat panel detector 86 between two curvilinear detector assemblies 88, 90, the resulting detector assembly 84 leverages the benefits of both flat panel detector technology and curvilinear detector technology while mitigating the negative aspects inherent in both types of detectors. For example, because the electrical charge from all of the detector elements on a given read line of a flat panel detector is fed onto the single readout circuit for that line, the sampling speed of a flat panel detector is lower than that of conventional curvilinear detector assemblies. However, because flat panel detector 86 is positioned at the center of the field of view, flat panel detector 86 acquires attenuation data corresponding to the slowest moving portion of the image. Also, because the manufacture of a flat panel detector is more cost effective than a curvilinear detector having a similar coverage area, use of flat panel detector 84 at the center of detector assembly 84 reduces the overall cost of detector assembly 84 while allowing for increased coverage in the z-direction 112 (i.e., along the patient axis). The longer lag or afterglow inherent in the use of flat panel detectors is also mitigated when by positioning flat panel detector 84 between curvilinear detector assemblies 88, 90. Finally, the limited dynamic range of a flat panel detector may be mitigated through the use of a second flat panel detector, such as second flat panel detector 148, for example. Detector assembly 84 is particularly advantageous for use in cardiac CT imaging applications, as flat panel detector 84 provides the resolution and coverage desired for cardiac imaging.

Figure 14:
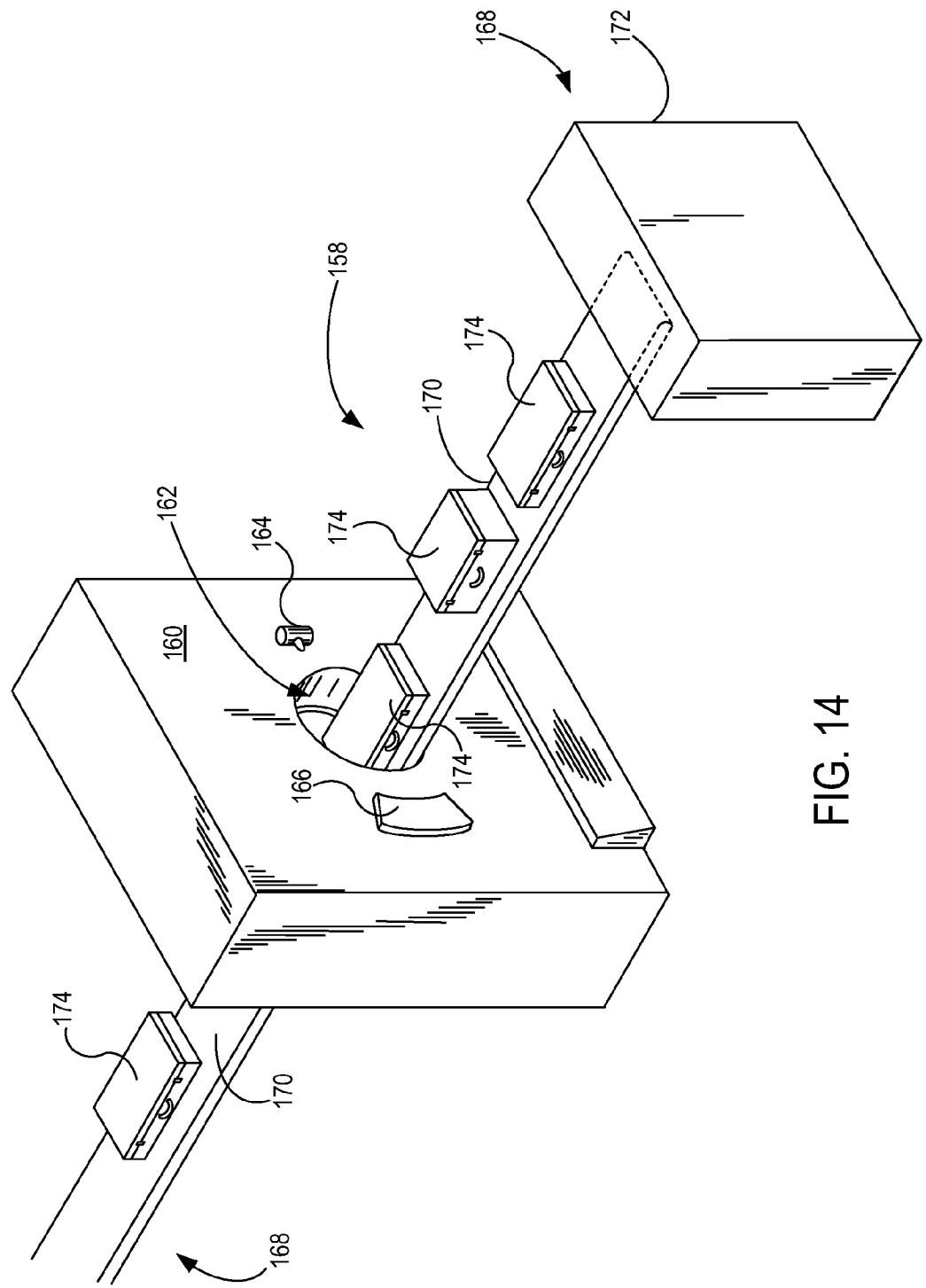
FIG. 14 is a pictorial view of a CT system for use with a non-invasive package inspection system.

Referring now to FIG. 14, package/baggage inspection system 158 includes a rotatable gantry 160 having an opening 162 therein through which packages or pieces of baggage may pass. The rotatable gantry 160 houses a high frequency electromagnetic energy source 164 as well as a detector assembly 166 having scintillator arrays comprised of scintillator cells similar to that shown in FIG. 3 or 4. A conveyor system 168 is also provided and includes a conveyor belt 170 supported by structure 172 to automatically and continuously pass packages or baggage pieces 174 through opening 162 to be scanned. Objects 174 are fed through opening 162 by conveyor belt 170, imaging data is then acquired, and the conveyor belt 170 removes the packages 174 from opening 162 in a controlled and continuous manner. As a result, postal inspectors, baggage handlers, and other security personnel may non-invasively inspect the contents of packages 174 for explosives, knives, guns, contraband, etc.

One skilled in the art will appreciate that embodiments of the invention may be interfaced to and controlled by a computer readable storage medium having stored thereon a computer program. The computer readable storage medium includes a plurality of components such as one or more of electronic components, hardware components, and/or computer software components. These components may include one or more computer readable storage media that generally stores instructions such as software, firmware and/or assembly language for performing one or more portions of one or more implementations or embodiments of a sequence. These computer readable storage media are generally non-transitory and/or tangible. Examples of such a computer readable storage medium include a recordable data storage medium of a computer and/or storage device. The computer readable storage media may employ, for example, one or more of a magnetic, electrical, optical, biological, and/or atomic data storage medium. Further, such media may take the form of, for example, floppy disks, magnetic tapes, CD-ROMs, DVD-ROMs, hard disk drives, and/or electronic memory. Other forms of non-transitory and/or tangible computer readable storage media not list may be employed with embodiments of the invention.

A number of such components can be combined or divided in an implementation of a system. Further, such components may include a set and/or series of computer instructions written in or implemented with any of a number of programming languages, as will be appreciated by those skilled in the art. In addition, other forms of computer readable media such as a carrier wave may be employed to embody a computer data signal representing a sequence of instructions that when executed by one or more computers causes the one or more computers to perform one or more portions of one or more implementations or embodiments of a sequence.

Therefore, in accordance with one embodiment, an x-ray detector assembly includes a first curvilinear detector assembly comprising a first plurality of detector modules, a second curvilinear detector assembly comprising a second plurality of detector modules, and a first flat panel digital projection detector arranged between the first and second curvilinear detector assemblies such that a first end of the first flat panel digital projection detector is coupled to an inner end of the first curvilinear detector assembly and a second end of the first flat panel digital projection detector is coupled to an inner end of the second curvilinear detector assembly.

In accordance with another embodiment, a method of manufacturing a detector assembly includes providing a first flat panel detector having a top surface configured to face an x-ray source, a first side surface extending from the top surface of the first flat panel detector to a bottom surface opposite the top surface, and a second side surface opposite the first side surface and extending from the top surface to the bottom surface. The method also includes providing a first curvilinear detector array having a plurality of detectors arranged therein, the first curvilinear detector array comprising a top surface configured to face the x-ray source, and aligning the first curvilinear detector array with the first flat panel detector such that an edge of the top surface of the first curvilinear detector abuts the first side surface of the first flat panel detector. Further, the method includes providing a second curvilinear detector array having a plurality of detectors arranged therein, the second curvilinear detector array comprising a top surface configured to face the x-ray source, and aligning the second curvilinear detector array with the first flat panel detector such that an edge of the top surface of the second curvilinear detector abuts the second side surface of the first flat panel detector.

In accordance with yet another embodiment, a CT system includes a rotatable gantry having an opening therein for receiving an object to be scanned and a table positioned within the opening of the rotatable gantry and moveable through the opening in a z-direction. The CT system also includes an x-ray source coupled to the rotatable gantry and configured to project a beam of x-rays toward the object to be scanned, and a detector assembly positioned to receive the beam of x-rays from the x-ray source. The detector assembly includes a first curvilinear detector assembly comprising a plurality of detectors, a second curvilinear detector assembly comprising a plurality of detectors, and a first flat panel digital detector arranged between the first and second curvilinear detector assemblies such that a first end of the first flat panel digital detector is coupled to an inner end of the first curvilinear detector assembly and a second end of the first flat panel detector is coupled to an inner end of the second curvilinear detector assembly.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An x-ray detector assembly comprising:
  a first curvilinear detector assembly comprising a first plurality of detector modules;
  a second curvilinear detector assembly comprising a second plurality of detector modules; and
  a first flat panel digital projection detector arranged between the first and second curvilinear detector assemblies such that a first end of the first flat panel digital projection detector is coupled to an inner end of the first curvilinear detector assembly and a second end of the first flat panel projection digital detector is coupled to an inner end of the second curvilinear detector assembly.

2. The x-ray detector assembly of claim 1 further comprising a second flat panel digital projection detector substantially aligned with the first flat panel digital projection detector in an x-ray penetration direction and spaced apart from the first flat panel digital projection detector in the x-ray penetration direction.

3. The x-ray detector assembly of claim 2 wherein the first flat panel digital projection detector has a coverage area at least equal to a coverage area of the second flat panel digital projection detector.

4. The x-ray detector assembly of claim 2 wherein the second flat panel digital projection detector is mounted on guide rails such that the second flat panel digital projection detector is moveable between a first position and a second position;
  wherein, when in the first position, the second flat panel digital projection detector is aligned with the first flat panel digital projection detector such that x-rays emitting from an x-ray source and passing through the second flat panel digital projection detector in the x-ray penetration direction impinge upon the first flat panel digital projection detector; and
  wherein, when in the second position, the second flat panel digital projection detector is misaligned with the first flat panel digital projection detector such that x-rays emitting from the x-ray source in the x-ray penetration direction impinge upon the first flat panel digital projection detector without passing through the second flat panel digital projection detector.

5. The x-ray detector assembly of claim 2 further comprising a notch filter comprising an x-ray attenuating material selected to filter x-rays within a given energy band.

6. The x-ray detector assembly of claim 5 wherein the notch filter is positioned between the first flat panel digital projection detector and the second flat panel digital projection detector in the x-ray penetration direction.

7. The x-ray detector assembly of claim 2 wherein the first flat panel digital projection detector is configured to absorb high-energy x-rays; and
  wherein the second flat panel digital projection detector is configured to absorb low-energy x-rays.

8. The x-ray detector assembly of claim 1 wherein the plurality of detector modules of the first and second curvilinear detector assemblies have a width in a channel direction of approximately 16 mm; and
  wherein the first flat panel digital projection detector has a width in the channel direction of approximately 20 cm.

9. A method of manufacturing a detector assembly comprising:
providing a first flat panel detector comprising:
a top surface configured to face an x-ray source;
a first side surface extending from the top surface of the first flat panel detector to a bottom surface opposite the top surface; and
a second side surface opposite the first side surface and extending from the top surface to the bottom surface;
providing a first curvilinear detector array having a plurality of detectors arranged therein, the first curvilinear detector array comprising a top surface configured to face the x-ray source;
aligning the first curvilinear detector array with the first flat panel detector such that an edge of the top surface of the first curvilinear detector abuts the first side surface of the first flat panel detector;
providing a second curvilinear detector array having a plurality of detectors arranged therein, the second curvilinear detector array comprising a top surface configured to face the x-ray source; and
aligning the second curvilinear detector array with the first flat panel detector such that an edge of the top surface of the second curvilinear detector abuts the second side surface of the first flat panel detector.

10. The method of manufacturing of claim 9 further comprising positioning a second flat panel detector to overlap the first flat panel detector in an x-ray penetration direction such that x-rays emitting from the x-ray source and passing through the second flat panel detector in the x-ray penetration direction impinge upon the first flat panel detector.

11. The method of manufacturing of claim 10 further comprising mounting the second flat panel detector on guide rails such that the second flat panel detector may be selectively moved to a non-overlapping position with respect to the first flat panel detector wherein x-rays emitting from the x-ray source in the x-ray penetration direction impinge upon the first flat panel detector without passing through the second flat panel detector.

12. The method of manufacturing of claim 10 further comprising positioning a notch filter between the first and second flat panel detectors in the x-ray penetration direction.

13. The method of manufacturing of claim 9 wherein providing the first flat panel detector comprises providing a digital projection radiographic detector having a coverage area at least equal in size to a complete projection of an average adult heart.

14. A computed tomography (CT) system comprising:
a rotatable gantry having an opening therein for receiving an object to be scanned;
a table positioned within the opening of the rotatable gantry and moveable through the opening in a z-direction;
an x-ray source coupled to the rotatable gantry and configured to project a beam of x-rays toward the object to be scanned; and
a detector assembly positioned to receive the beam of x-rays from the x-ray source, the detector assembly comprising:
a first curvilinear detector assembly comprising a plurality of detectors;
a second curvilinear detector assembly comprising a plurality of detectors; and
a first flat panel digital detector arranged between the first and second curvilinear detector assemblies such that a first end of the first flat panel digital detector is coupled to an inner end of the first curvilinear detector assembly and a second end of the first flat panel detector is coupled to an inner end of the second curvilinear detector assembly.

15. The CT system of claim 14 further comprising a second flat panel digital detector positioned above the first flat panel digital detector in an x-ray penetration direction such that a plurality of x-rays of the beam of x-rays pass through the second flat panel digital detector prior to impinging upon the first flat panel digital detector.

16. The CT system of claim 15 further comprising a notch filter positioned between the first flat panel digital detector and the second flat panel digital detector.

17. The CT system of claim 15 wherein the second flat panel digital detector has a thickness in an x-ray penetration direction that is less than a thickness of the first flat panel digital detector.

18. The CT system of claim 15 wherein the first flat panel digital detector comprises a first scintillating material configured to absorb high-energy x-rays; and
wherein the second flat panel digital detector comprises a second scintillating material configured to absorb low-energy x-rays.

19. The CT system of claim 14 wherein the first flat panel digital detector has a coverage area that is large enough to acquire projection data for a whole adult heart during one rotation of the rotatable gantry.

20. The CT system of claim 14 further comprising:
a data acquisition system configured to receive projection data from the first and second curvilinear detector assemblies and the first flat panel digital detector; and
an image reconstructor coupled to the data acquisition system to receive the projection data, wherein the image reconstructor is programmed to apply calibration and corrections to the projection data to account for interference between the first and second curvilinear detector assemblies and the first flat panel digital detector.

* * * * *